(12) United States Patent
Vella et al.

(10) Patent No.: US 8,768,234 B2
(45) Date of Patent: Jul. 1, 2014

(54) DELIVERY APPARATUS AND METHOD

(75) Inventors: Sarah J. Vella, Windsor (CA); Nan-Xing Hu, Oakville (CA); Yu Liu, Mississauga (CA); Richard A. Klenkler, Oakville (CA)

(73) Assignee: Xerox Corporation, Norwalk, CT (US)

( * ) Notice: Subject to any disclaimer, the term of this patent is extended or adjusted under 35 U.S.C. 154(b) by 265 days.

(21) Appl. No.: 13/279,981

(22) Filed: Oct. 24, 2011

(65) Prior Publication Data
US 2013/0101327 A1  Apr. 25, 2013

(51) Int. Cl.
*G03G 21/00* (2006.01)
(52) U.S. Cl.
USPC .......................... 399/346; 399/100; 399/176
(58) Field of Classification Search
USPC ......................... 399/100, 176, 346
See application file for complete search history.

(56) References Cited

U.S. PATENT DOCUMENTS

| | | | |
|---|---|---|---|
| 3,121,006 A | 2/1964 | Middleton et al. | |
| 4,387,980 A | 6/1983 | Ueno et al. | |
| 4,435,074 A | 3/1984 | Midorikawa et al. | |
| 4,464,450 A | 8/1984 | Teuscher | |
| 4,587,189 A | 5/1986 | Hor et al. | |
| 4,664,995 A | 5/1987 | Horgan et al. | |
| 4,921,773 A | 5/1990 | Melnyk et al. | |
| 5,069,993 A | 12/1991 | Robinette et al. | |
| 5,384,929 A | 1/1995 | Smith | |
| 5,499,089 A | 3/1996 | Tsukamoto et al. | |
| 5,646,718 A | 7/1997 | Suwa et al. | |
| 5,756,245 A | 5/1998 | Esteghamatian et al. | |
| 6,434,357 B1 * | 8/2002 | Maul et al. | 399/325 |
| 6,582,222 B1 * | 6/2003 | Chen et al. | 399/330 |
| 6,869,918 B2 | 3/2005 | Cornelius | |
| 7,428,402 B2 | 9/2008 | Hays et al. | |
| 7,526,243 B2 | 4/2009 | Zaman et al. | |
| 7,580,655 B2 | 8/2009 | Nukada et al. | |
| 7,725,069 B2 | 5/2010 | Kawahara et al. | |
| 7,734,242 B2 * | 6/2010 | Hatakeyama et al. | 399/346 |
| 7,877,054 B1 | 1/2011 | Thayer et al. | |
| 7,881,651 B2 | 2/2011 | Watanabe | |
| 7,960,082 B2 | 6/2011 | Aziz et al. | |
| 8,600,281 B2 | 12/2013 | Hu et al. | |
| 2003/0049555 A1 | 3/2003 | Sakon et al. | |
| 2003/0118372 A1 | 6/2003 | Kitano et al. | |
| 2005/0163527 A1 | 7/2005 | Tombs | |
| 2009/0087213 A1 | 4/2009 | Takaya et al. | |
| 2009/0162092 A1 | 6/2009 | Hoshio | |
| 2009/0185821 A1 | 7/2009 | Iwamoto et al. | |
| 2009/0220876 A1 | 9/2009 | De Jong et al. | |

(Continued)

FOREIGN PATENT DOCUMENTS

JP      2002357983 A     12/2002

OTHER PUBLICATIONS

U.S. Appl. No. 13/286,905, filed Nov. 1, 2011.
U.S. Appl. No. 13/020,738, filed Feb. 3, 2011.

(Continued)

*Primary Examiner* — Ryan Walsh
(74) *Attorney, Agent, or Firm* — Hoffman Warnick LLC

(57) ABSTRACT

There is described a delivery member for use in an image forming apparatus. The delivery member includes a support member, an inner layer comprising a elastomeric matrix and a functional material dispersed therein, the inner layer disposed on the support member and an outer layer disposed on the inner layer. A method for manufacturing the delivery member and its function are described.

17 Claims, 6 Drawing Sheets

(56) References Cited

U.S. PATENT DOCUMENTS

| | | |
|---|---|---|
| 2010/0189461 A1 | 7/2010 | Shintani et al. |
| 2011/0033798 A1 | 2/2011 | Kim et al. |
| 2011/0206430 A1 | 8/2011 | Arai et al. |

OTHER PUBLICATIONS

U.S. Appl. No. 12/845,662, filed Jul. 28, 2010.
U.S. Appl. No. 13/192, 252, filed Jul. 27, 2011.
U.S. Appl. No. 13/192,215, filed Jul. 27, 2011.
U.S. Appl. No. 13/533,475, Notice of Allowance and Fees Due, XRX-0081, Dec. 9, 2013, 20 pages.
U.S. Appl. No. 13/437,472, Office Action, XRX-0075, Dec. 20, 2013, 18 pages.
Sanghera, U.S. Appl. No. 13/354,022, Office Action dated Aug. 8, 2013, (XRX-0071), 25 pages.
U.S. Appl. No. 13/426,836, Ex Parte Quayle Action dated Mar. 20, 2014, XRX-0078, 18 pages.
U.S. Appl. No. 13/437,472, Notice of Allowance & Fees Due, Mar. 31, 2014, 7 pages.
U.S. Appl. No. 13/326,414, Office Action, Mar. 28, 2014, 19 pages.

\* cited by examiner

DELIVERY APPARATUS AND METHOD

BACKGROUND

1. Field of Use

This disclosure is generally directed to the delivery of a functional material or lubricant to the surface of imaging members, photoreceptors, photoconductors, and the like.

2. Background

In electrophotography or electrophotographic printing, the charge retentive surface, typically known as a photoreceptor, is electrostatically charged, and then exposed to a light pattern of an original image to selectively discharge the surface in accordance therewith. The resulting pattern of charged and discharged areas on the photoreceptor form an electrostatic charge pattern, known as a latent image, conforming to the original image. The latent image is developed by contacting it with a finely divided electrostatically attractable powder known as toner. Toner is held on the image areas by the electrostatic charge on the photoreceptor surface. Thus, a toner image is produced in conformity with a light image of the original being reproduced or printed. The toner image may then be transferred to a substrate or support member (e.g., paper) directly or through the use of an intermediate transfer member, and the image affixed thereto to form a permanent record of the image to be reproduced or printed. Subsequent to development, excess toner left on the charge retentive surface is cleaned from the surface. The process is useful for light lens copying from an original or printing electronically generated or stored originals such as with a raster output scanner (ROS), where a charged surface may be imagewise discharged in a variety of ways.

The described electrophotographic copying process is well known and is commonly used for light lens copying of an original document. Analogous processes also exist in other electrophotographic printing applications such as, for example, digital laser printing and reproduction where charge is deposited on a charge retentive surface in response to electronically generated or stored images.

To charge the surface of a photoreceptor, a contact type charging device has been used, such as disclosed in U.S. Pat. No. 4,387,980 and U.S. Pat. No. 7,580,655, which are incorporated herein by reference in their entirety. The contact type charging device, also termed "bias charge roll" (BCR) includes a conductive member which is supplied a voltage from a power source with a D.C. voltage superimposed with an A.C. voltage of no less than twice the level of the D.C. voltage. The charging device contacts the image bearing member (photoreceptor) surface, which is a member to be charged. The outer surface of the image bearing member is charged at the contact area. The contact type charging device charges the image bearing member to a predetermined potential.

Electrophotographic photoreceptors can be provided in a number of forms. For example, the photoreceptors can be a homogeneous layer of a single material, such as vitreous selenium, or it can be a composite layer containing a photoconductive layer and another material. In addition, the photoreceptor can be layered. Multilayered photoreceptors or imaging members have at least two layers, and may include a substrate, a conductive layer, an optional undercoat layer (sometimes referred to as a "charge blocking layer" or "hole blocking layer"), an optional adhesive layer, a photogenerating layer (sometimes referred to as a "charge generation layer," "charge generating layer," or "charge generator layer"), a charge transport layer, and an optional overcoating layer in either a flexible belt form or a rigid drum configuration. In the multilayer configuration, the active layers of the photoreceptor are the charge generation layer (CGL) and the charge transport layer (CTL). Enhancement of charge transport across these layers provides better photoreceptor performance. Multilayered flexible photoreceptor members may include an anti-curl layer on the backside of the substrate, opposite to the side of the electrically active layers, to render the desired photoreceptor flatness.

To further increase the service life of the photoreceptor, use of overcoat layers has also been implemented to protect photoreceptors and improve performance, such as wear resistance. However, these low wear overcoats are associated with poor image quality due to A-zone deletion in a humid environment as the wear rates decrease to a certain level. In addition, high torque associated with low wear overcoats in A-zone also causes severe issues with BCR charging systems, such as motor failure and blade damage. As a result, use of a low wear overcoat with BCR charging systems is still a challenge, and there is a need to find ways to increase the life of the photoreceptor.

SUMMARY

Disclosed herein is a delivery member for use in an image forming apparatus. The delivery member comprises a support member, an inner layer comprising an elastomeric matrix and a functional material dispersed therein, the inner layer disposed on the support member and an outer layer disposed on the inner layer.

Disclosed herein is an image forming apparatus comprising an imaging member having a charge retentive-surface for developing an electrostatic latent image thereon. The imaging member comprises a substrate and a photoconductive member disposed on the substrate. The image forming apparatus includes a charging unit for applying an electrostatic charge on the imaging member to a predetermined electric potential and a delivery member in contact with the surface of the imaging member or the surface of the charging unit. The delivery member comprises a support member, an inner layer comprising a elastomeric matrix and a functional material dispersed therein, the inner layer disposed on the support member and an outer layer disposed on the inner layer.

Disclosed herein is a delivery member for use in an image forming apparatus. The delivery member comprises a support member, an inner layer disposed on the support member and an outer layer disposed on the inner layer. The inner layer comprises a elastomeric matrix and a functional material dispersed therein. The inner layer comprises pores having a size of from about 5 microns to about 25 microns. The outer layer comprises pores having a size of from about less than about 500 nm.

BRIEF DESCRIPTION OF THE DRAWINGS

The accompanying drawings, which are incorporated in and constitute a part of this specification, illustrate several embodiments of the present teachings and together with the description, serve to explain the principles of the present teachings.

Figure 1:
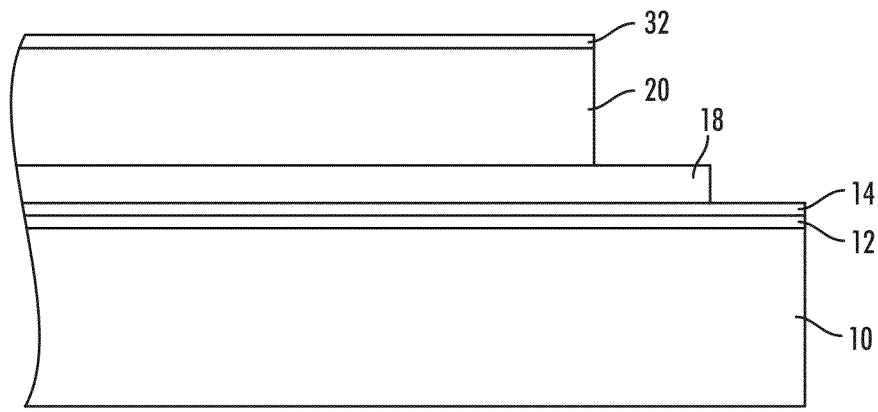
FIG. 1 is a is a cross-sectional view of an imaging member in a drum configuration according to the present embodiments.

It should be noted that some details of the figures have been simplified and are drawn to facilitate understanding of the embodiments rather than to maintain strict structural accuracy, detail, and scale.

DESCRIPTION OF THE EMBODIMENTS

In the following description, reference is made to the chemical formulas that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. −1, −2, −3, −10, −20, −30, etc.

The disclosed embodiments are directed generally to delivery apparatus for applying a layer of a functional material that act as a lubricant on an imaging member surface. The layer of functional material acts as a barrier against moisture and/or surface contaminants thereby protecting the surface of the imaging member. The apparatus provides improved wear resistance, low friction, and reduced image defects due to deletion in high humidity conditions which leads to improved xerographic performance in imaging members.

A long life photoreceptor (P/R) enables significant cost reduction. Generally P/R life extension is achieved with a wear-resistant overcoat. However, wear resistant overcoats are associated with an increase in A-zone deletion (a printing defect that occurs at high humidity). Most organic photoreceptor materials require a minimal wear rate of 2 nm/Kcycle (Scorotron charging system) or from about 5 nm/Kcycle to about 10 nm/Kcycle (BCR charging system) in order to suppress A-zone deletion. In addition, wear-resistant overcoats cause a higher torque that results in issues with BCR (bias charging roller) charging systems, such as motor failure and blade damage (which results in streaking of toner in prints).

FIG. 1 is an exemplary embodiment of a multilayered electrophotographic imaging member or photoreceptor having a drum configuration. The substrate may further be in a cylinder configuration. As can be seen, the exemplary imaging member includes a rigid support substrate 10, an electrically conductive ground plane 12, an undercoat layer 14, a charge generation layer 18 and a charge transport layer 20. An optional overcoat layer 32 disposed on the charge transport layer 20 may also be included. The substrate 10 may be a material selected from the group consisting of a metal, metal alloy, aluminum, zirconium, niobium, tantalum, vanadium, hafnium, titanium, nickel, stainless steel, chromium, tungsten, molybdenum, and mixtures thereof. The substrate 10 may also comprise a material selected from the group consisting of a metal, a polymer, a glass, a ceramic, and wood.

The charge generation layer 18 and the charge transport layer 20 form an imaging layer described here as two separate layers. In an alternative to what is shown in the figure, the charge generation layer 18 may also be disposed on top of the charge transport layer 20. It will be appreciated that the functional components of these layers may alternatively be combined into a single layer.

Figure 2:
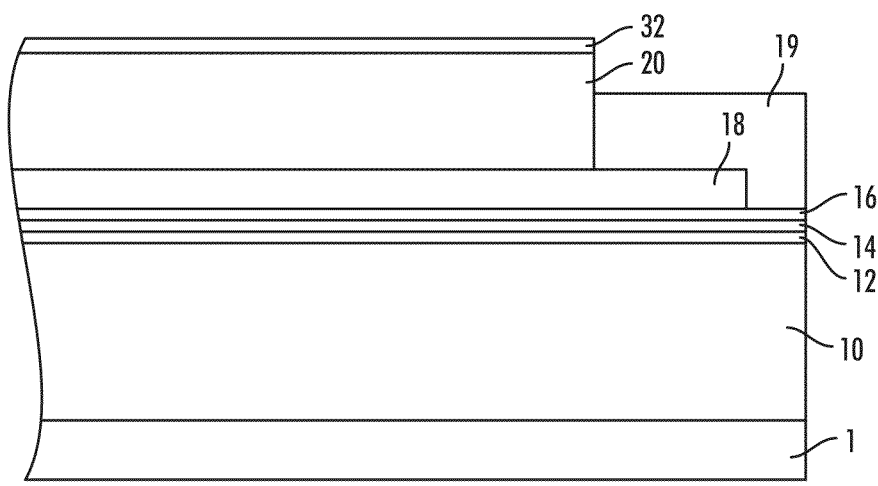
FIG. 2 is a cross-sectional view of an imaging member in a belt configuration according to the present embodiments.

FIG. 2 shows an imaging member or photoreceptor having a belt configuration according to the embodiments. As shown, the belt configuration is provided with an anti-curl back coating 1, a supporting substrate 10, an electrically conductive ground plane 12, an undercoat layer 14, an adhesive layer 16, a charge generation layer 18, and a charge transport layer 20. An optional overcoat layer 32 and ground strip 19 may also be included. An exemplary photoreceptor having a belt configuration is disclosed in U.S. Pat. No. 5,069,993, which is hereby incorporated by reference in its entirety.

As discussed above, an electrophotographic imaging member generally comprises at least a substrate layer, an imaging layer disposed on the substrate and an optional overcoat layer disposed on the imaging layer. In further embodiments, the imaging layer comprises a charge generation layer disposed on the substrate and the charge transport layer disposed on the charge generation layer. In other embodiments, an undercoat layer may be included and is generally located between the substrate and the imaging layer, although additional layers may be present and located between these layers. The imaging member may also include an anti-curl back coating layer in certain embodiments. The imaging member can be employed in the imaging process of electrophotography, where the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. The radiation selectively dissipates the charge on the illuminated areas of the photoconductive insulating layer while leaving behind an electrostatic latent image. This electrostatic latent image may then be developed to form a visible image by depositing charged particles of same or opposite polarity on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

Common print quality issues are strongly dependent on the quality and interaction of these photoreceptor layers. For example, when a photoreceptor is used in combination with a contact charger and a toner obtained by chemical polymerization (polymerization toner), image quality may be deteriorated due to a surface of the photoreceptor being stained with a discharge product produced in contact charging or the polymerization toner remaining after a cleaning step. Still further, repetitive cycling causes the outermost layer of the photoreceptor to experience a high degree of frictional contact with other machine subsystem components used to clean and/or prepare the photoreceptor for imaging during each cycle. When repeatedly subjected to cyclic mechanical interactions against the machine subsystem components, a photoreceptor can experience severe frictional wear at the outermost organic photoreceptor layer surface that can greatly reduce the useful life of the photoreceptor. Ultimately, the resulting wear impairs photoreceptor performance and thus image quality. Another type of common image defect is thought to result from the accumulation of charge somewhere in the photoreceptor. Consequently, when a sequential image is printed, the accumulated charge results in image density changes in the current printed image that reveals the previously printed image. In the xerographic process spatially varying amounts of positive charges from the transfer station find themselves on the photoreceptor surface. If this variation is large enough it will manifest itself as a variation in the image potential in the following xerographic cycle and print out as a defect.

A conventional approach to photoreceptor life extension is to apply an overcoat layer with wear resistance. For bias charge roller (BCR) charging systems, overcoat layers are associated with a trade-off between A-zone deletion (i.e. an image defect occurring in A-zone: 28° C., 85% RH) and photoreceptor wear rate. For example, most organic photoconductor (OPC) materials sets require a certain level of wear rate in order to suppress A-zone deletion, thus limiting the life of a photoreceptor. The present embodiments, however, have demonstrated a decrease in wear rate of a photoreceptor while maintaining the image quality of the photoreceptor, such as decreased image deletions. The present embodiments provide photoreceptor technology for BCR charging systems with a significantly expanded life.

Disclosed herein is a delivery device and system that provide better delivery of the functional material or lubricant to the surface of the imaging device, typically a photoreceptor. The delivery roller comprises two layers: an inner layer that functions as a reservoir for the functional material and an outer layer that functions to control the delivery of the functional material. In an embodiment there is provided a double layer roller where the inner layer comprises a functional material dispersed in an elastomeric matrix, and the outer layer comprising an elastomer. The outer layer has smaller pores (less than about 1 μm, or less than about 500 nm or less than about 300 nm) than the inner layer (pores are from about 1 micron to about 50 microns, or the pores are from about 8 microns to about 20 microns, or the pores are from about 10 microns to about 17 microns). The pores of the inner layer are filled with functional material. The smaller pores of the outer layer control the diffusion of the functional material from the inner layer. The double layer roller applies an ultra-thin film of functional material to the surface of a photoreceptor either directly or indirectly which: i) reduces torque between the P/R and the cleaning blade and ii) eliminates A zone deletions, both of which improve image quality.

The present embodiments employ a delivery apparatus and system to deliver a layer of functional materials onto the photoreceptor surface either directly or through a charging roller. The functional material is applied to the photoreceptor surface and acts as lubricant and or a barrier against moisture and surface contaminants and improves xerographic performance in high humidity conditions, such as, for example, A-zone environment. The ultra-thin layer may be provided on a nano-scale or molecular level.

In embodiments, a functional material is continuously delivered on the photoreceptor to form an ultra-thin layer of lubricant to protect machine subsystem components through reducing friction between the cleaning blade and the photoreceptor surface or at the contact interface between the photoreceptor surface and other relevant components. This lubricant further reduces the resultant torque and vibration so that the actuator and involved transmission mechanisms can move the photoreceptor or other relevant components in a smoother way. Therefore, the lubricant improves the printed image quality, which may be deteriorated due to aforementioned reasons, and further protects these components and extends their service life.

In embodiments, there is provided an image forming apparatus that includes a delivery member for delivering functional materials onto a photoreceptor. The apparatus typically comprises an imaging member; a charging unit comprising a charging roller disposed in contact with the surface of the imaging member; and a delivery unit disposed in contact with the surface of the charging roller, wherein the delivery unit applies a layer of functional material to the surface of the charging roller and the charging roller in turn applies a layer of the functional material onto the surface of the imaging member. In an embodiment, the delivery roller delivers a functional material directly to the surface of the imaging member.

Figure 3:
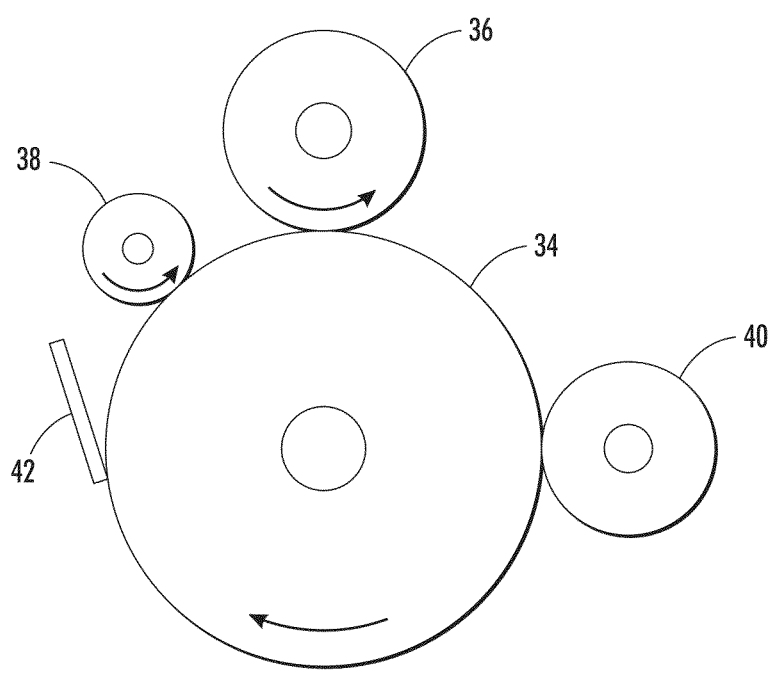
FIG. 3 is a cross-sectional view of a system implementing a delivery member according to the present embodiments.

FIGS. 3-6 illustrate delivery members according to the present embodiments. In FIG. 3, there is illustrated an image-forming apparatus in a BCR charging system. As shown, the image-forming apparatus comprises a photoreceptor 34, a BCR 36 and a delivery member 38. The delivery member 38 contacts the photoreceptor 34 to deliver an ultra-thin layer of a functional material onto the surface of the photoreceptor 34. Subsequently, the photoreceptor 34 is substantially uniformly charged by the BCR 36 to initiate the electrophotographic reproduction process. The charged photoreceptor is then exposed to a light image to create an electrostatic latent image on the photoreceptive member (not shown). This latent image is subsequently developed into a visible image by a toner developer 40. Thereafter, the developed toner image is transferred from the photoreceptor member through a record medium to a copy sheet or some other image support substrate to which the image may be permanently affixed for producing a reproduction of the original document (not shown). The photoreceptor surface is generally then cleaned with a cleaner 42 to remove any residual developing material therefrom, in preparation for successive imaging cycles.

Figure 4:
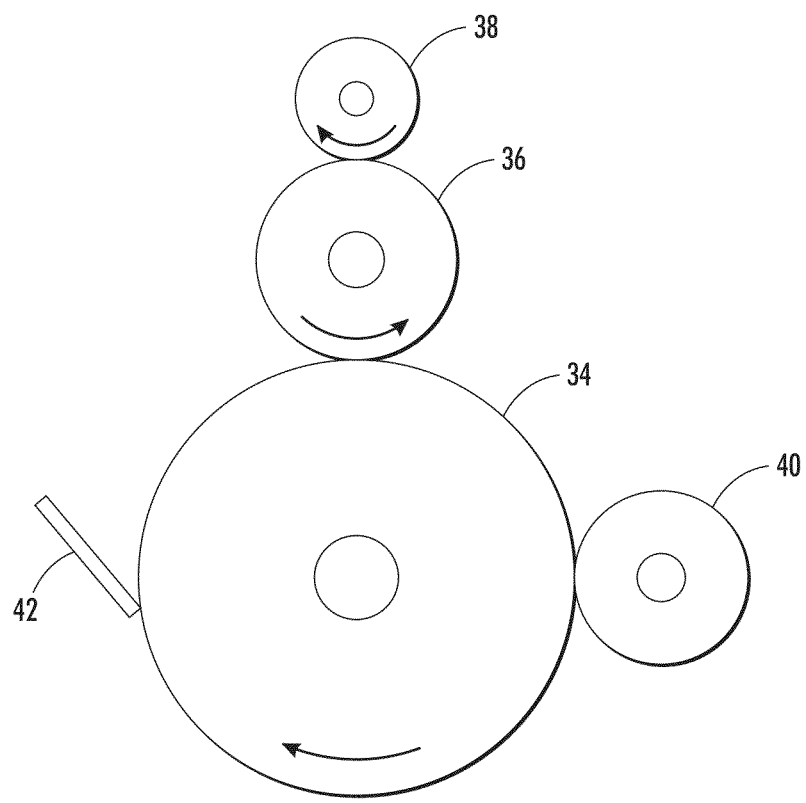
FIG. 4 is an alternative cross-sectional view of a system implementing a delivery member according to the present embodiments.

In an alternative configuration, as shown in FIG. 4, the delivery member 38 contacts the BCR 36 to deliver an ultra-thin layer of the functional material onto the surface of the BCR 36. The BCR 36, in turn, transfers the functional material onto the surface of the photoreceptor 34. The delivery member may be integrated into a xerographic printing system in various configurations and positions. As can be seen, as the overcoated photoreceptor drum 34 rotates, the delivery member 38 impregnated with the functional material delivers the functional materials to the surface of the overcoated photoreceptor 34 (FIG. 3), or to the surface of the BCR (FIG. 4), through contact diffusion. For example, the functional material dispersed therein can diffuse to the surface of the delivery member 38. As with the prior embodiment, the photoreceptor 34 is substantially uniformly charged by the BCR 36 to initiate the electrophotographic reproduction process. The charged photoreceptor is then exposed to a light image to create an electrostatic latent image on the photoreceptive member (not shown). This latent image is subsequently developed into a visible image by a toner developer 40. Thereafter, the developed toner image is transferred from the photoreceptor member through a record medium to a copy sheet or some other image support substrate to which the image may be permanently affixed for producing a reproduction of the original document (not shown). The photoreceptor surface is generally then cleaned with a cleaner 42 to remove any residual developing material therefrom, in preparation for successive imaging cycles.

Figure 5:
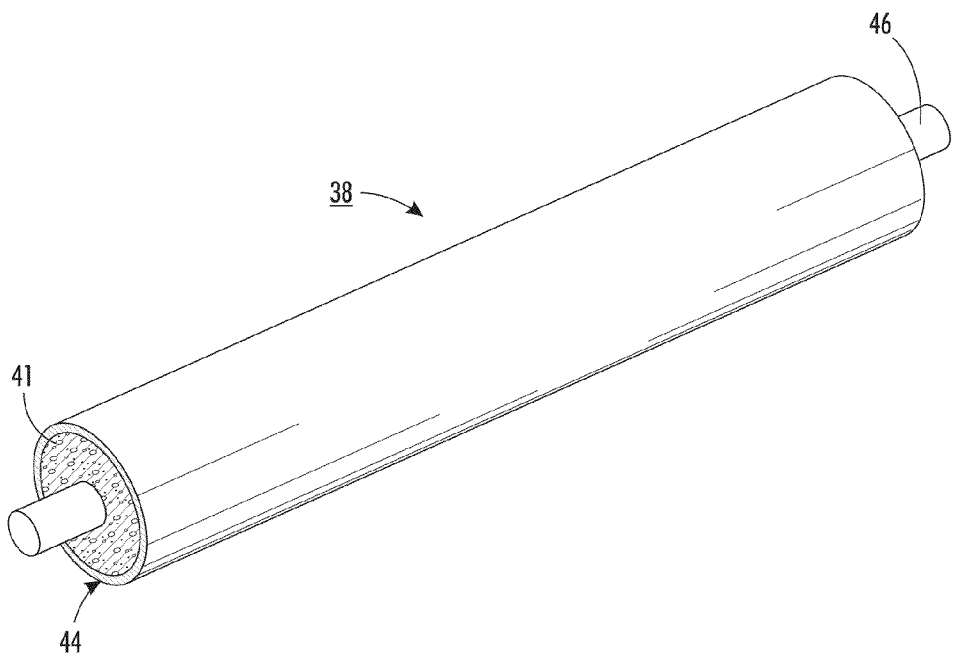
FIG. 5 is a side view of a delivery member according to the present embodiments.
Figure 6:
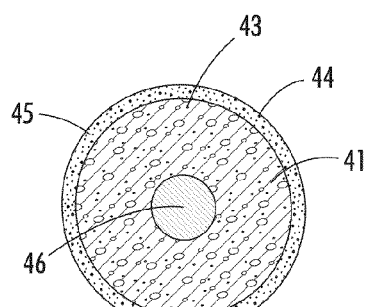
FIG. 6 is a cross-sectional view of a delivery member according to the present embodiments.

FIG. 5 illustrates the delivery member 38 according to the present embodiments. FIG. 6 is a cross-section of the delivery member shown in FIG. 5. The delivery member 38 comprises a dual layer comprising an inner layer 41 and an outer layer 44. The inner layer 41 comprises an elastomeric matrix having pores 43 of a size from about 5 microns and about 25 microns. The pores 43 contain functional material. The inner layer 41 is disposed around a support member 46. An outer layer 44 is disposed over the inner layer 41. The outer layer 44 is an elastomeric material that contains pores 45 having a size less than 500 nm.

In embodiments, the support member 46 is a stainless steel rod. The support member 46 can further comprise a material selected from the group consisting of metal, metal alloy, plastic, ceramic, and glass, and mixtures thereof.

The diameter of the support member 46 and the thickness of the inner layer 41 may be varied depending on the application needs. In specific embodiments, the support member has a diameter of from about 3 mm to about 10 mm. In specific embodiments, the inner layer has a thickness of from about 20 μm to about 100 mm.

In the present embodiments, the functional material contained with pores 43 of the inner layer 41 is delivered to the surface of the outer layer 44. The functional material is transferred to the surface of the imaging member directly (FIG. 3) or indirectly through transfer to the BCR surface (FIG. 4). Delivery members fabricated according to the present embodiments have shown to contain sufficient quantities of the functional material to continuously supply an ultra-thin layer of the functional material to the surface of the BCR/photoreceptor.

In embodiments, the functional material can be an organic or inorganic compound, oligomer or polymer, or a mixture thereof. The functional materials may be in the form of liquid, wax, or gel, and a mixture thereof. The functional material may also be selected from the group consisting of a lubricant material, a hydrophobic material, an oleophobic material, an amphiphilic material, and mixtures thereof. Illustrative examples of functional materials may include, for example, a liquid material selected from the group consisting of hydrocarbons, fluorocarbons, mineral oil, synthetic oil, natural oil, and mixtures thereof. The functional materials may further contain a functional group that facilitates adsorption of the functional materials on the photoreceptor surface, and optionally a reactive group that can chemically modify the photoreceptor surface. For examples, the functional materials may comprise paraffinic compound, alkanes, fluoroalkanes, alkyl silanes, fluoroalkyl silanes alkoxy-silanes, siloxanes, glycols or polyglycols, mineral oil, synthetic oil, natural oil or mixture thereof.

In embodiments, the inner layer 41 may be comprised of a polymer selected from the group consisting of polysiloxanes, polyurethanes, polyesters, fluoro-silicones, polyolefin, fluoroelastomers, synthetic rubber, natural rubber, and mixtures thereof.

In embodiments, the outer layer 44 is a polymer selected from the group consisting of polysiloxane, silicones, polyurethane, polyester, fluoro-silicone, polyolefin, fluoroelastomer, synthetic rubber, natural rubber and mixtures thereof.

In embodiments, the inner layer 41 is an elastomeric material cast around the support member 46 by use of a mold. Thereafter, the elastomeric matrix is cured. The inner layer 41 is impregnated with a functional material, such as paraffin by immersion. After curing, the elastomeric matrix containing the functional material is extracted from the mold and the outer layer 44 is prepared by mixing a cross-linkable eleastomeric polymer and then casting the mixture onto the inner layer 41 by use of a mold. The elastomeric material is then cured to form the delivery member.

In a specific embodiment, the inner layer 41 is a paraffin-impregnated silicone cast around the support member 46. The inner layer 41 of paraffin-impregnated silicone is prepared by mixing paraffin into a cross-linkable polydimethylsiloxane (PDMS) and then casting the mixture onto the support member 46 by use of a mold. Thereafter, the PDMS is cured. The inner layer 41 is impregnated with a functional material, such as paraffin by immersion. After curing, the PDMS coated rod is extracted from the mold and the outer layer 44 is prepared by mixing a cross-linkable polydimethylsiloxane (PDMS) and then casting the mixture onto the inner layer 41 by use of a mold. In embodiments, the liquid cross-linkable PDMS is prepared from a two-component system, namely, a base agent and a curing agent. In further embodiments, the base agent and curing agent are present in a weight ratio of from about 50:1 to 2:1, or from about 20:1 to about 5:1 in both the inner and outer layers. In embodiments, the weight ratio of the functional material to the elastomeric material of the inner layer 41 is at a weight ratio of from about 1:10 to about 1:1, or from about 1:8 to about 1:1.5 or from about 1:7 to about 1:2.

The delivery member may be presented in a roll or have other configurations such as a web. The thickness of inner layer and outer layer may be varied. For example, the inner layer from about 1 mm to about 30 mm, or from about or from about 2 mm to about 20 μm or form about 3 mm to about 10 mm. The thickness of the outer layer is from about 0.1 microns to about 1 mm, or from about 0.2 microns to about 0.9 mm or from about 0.3 microns to about 0.07 mm. The delivery member may have a surface pattern comprising indentations or protrusions that have a shape selected from the group consisting of circles, rods, ovals, squares, triangles, polygons, and mixtures thereof.

In embodiments, the amount of functional material delivered onto the photoreceptor surface should be sufficient to retain the photoreceptor performance properties. The functional material can be present on the photoreceptor surface at various amount, for example, at a molecular level, or amount of from about 1 ng/kcycle/cm$^2$ to about 10 mg/kcycle/cm$^2$, or from about 10 ng/kcycle/cm$^2$ to about 1 μg/kcycle/cm$^2$, 25 μg/kcycle/cm$^2$ to about 5 mg/kcycle/cm$^2$. The present embodiments provide a system (OCL P/R with a delivery roll) that exhibits both reduced photoreceptor wear rate, as well as, reduced streaking and A-zone deletion in images as compared to a system without a delivery roll.

The description below describes embodiments of photoconductors

The Overcoat Layer

Other layers of the imaging member may include, for example, an optional over coat layer 32. An optional overcoat layer 32, if desired, may be disposed over the charge transport layer 20 to provide imaging member surface protection as well as improve resistance to abrasion. In embodiments, the overcoat layer 32 may have a thickness ranging from about 0.1 micrometer to about 15 micrometers or from about 1 micrometer to about 10 micrometers, or in a specific embodiment, about 3 micrometers to about 10 micrometers. These overcoating layers typically comprise a charge transport component and an optional organic polymer or inorganic polymer. These overcoating layers may include thermoplastic organic polymers or cross-linked polymers such as thermosetting resins, UV or e-beam cured resins, and the likes. The overcoat layers may further include a particulate additive such as metal oxides including aluminum oxide and silica, or low surface energy polytetrafluoroethylene (PTFE), and combinations thereof.

Any known or new overcoat materials may be included for the present embodiments. In embodiments, the overcoat layer may include a charge transport component or a cross-linked charge transport component. In particular embodiments, for example, the overcoat layer comprises a charge transport component comprised of a tertiary arylamine containing a substituent capable of self cross-linking or reacting with the polymer resin to form a cured composition. Specific examples of charge transport components suitable for overcoat layer comprise the tertiary arylamine with a general formula of

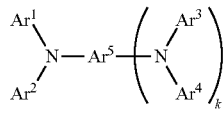

wherein $Ar^1$, $Ar^2$, $Ar^3$, and $Ar^4$ each independently represents an aryl group having about 6 to about 30 carbon atoms, $Ar^5$ represents aromatic hydrocarbon group having about 6 to about 30 carbon atoms, and k represents 0 or 1, and wherein at least one of $Ar^1$, $Ar^2$, $Ar^3$ $Ar^4$, and $Ar^5$ comprises a substituent selected from the group consisting of hydroxyl (—OH), a hydroxymethyl (—CH$_2$OH), an alkoxymethyl (—CH$_2$OR, wherein R is an alkyl having 1 to about 10 carbons), a hydroxylalkyl having 1 to about 10 carbons, and mixtures thereof. In other embodiments, $Ar^1$, $Ar^2$, $Ar^3$, and $Ar^4$ each independently represent a phenyl or a substituted phenyl group, and $Ar^5$ represents a biphenyl or a terphenyl group.

Additional examples of charge transport components which comprise a tertiary arylamine include the following:

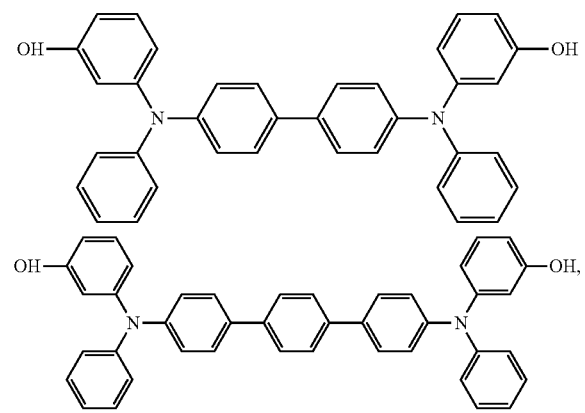

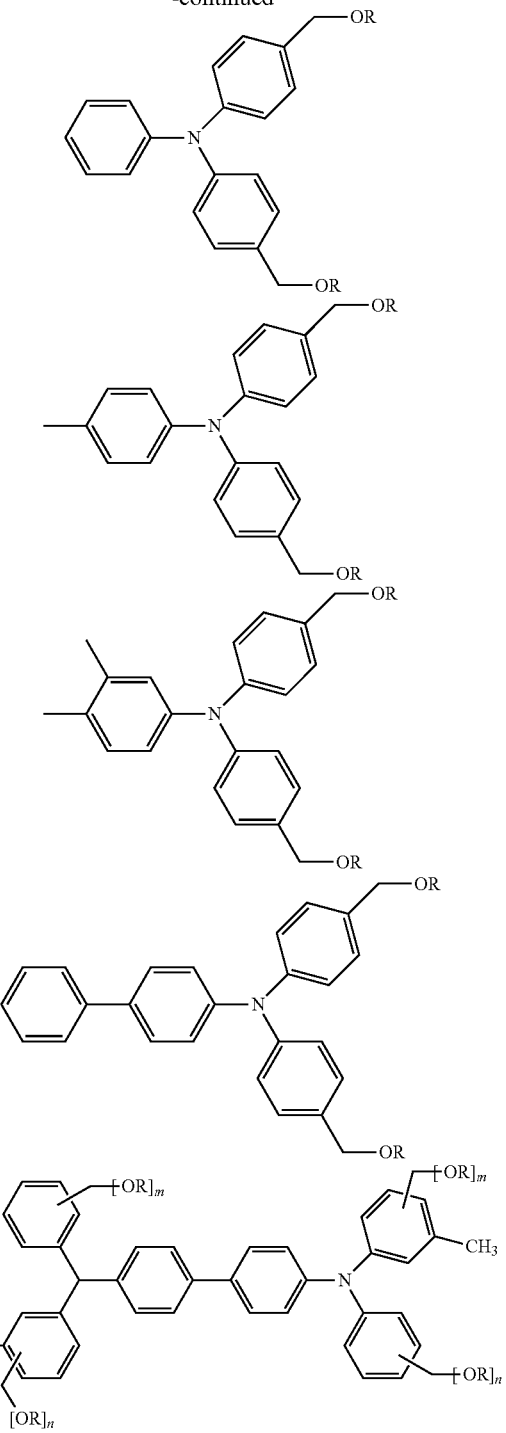

and the like, wherein R is a substituent selected from the group consisting of hydrogen atom, and an alkyl having from 1 to about 6 carbons, and m and n each independently represents 0 or 1, wherein m+n>1. In specific embodiments, the overcoat layer may include an additional curing agent to form a cured, crosslinked overcoat composition. Illustrative examples of the curing agent may be selected from the group consisting of a melamine-formaldehyde resin, a phenol resin, an isocyalate or a masking isocyalate compound, an acrylate resin, a polyol resin, or mixtures thereof. In embodiments, the crosslinked overcoat composition has an average modulus ranging from about 3 GPa to about 5 GPa, as measured by nano-indentation method using, for example, nanomechanical test instruments manufactured by Hysitron Inc. (Minneapolis, Minn.).

The Substrate

The photoreceptor support substrate 10 may be opaque or substantially transparent, and may comprise any suitable organic or inorganic material having the requisite mechanical properties. The entire substrate can comprise the same material as that in the electrically conductive surface, or the electrically conductive surface can be merely a coating on the substrate. Any suitable electrically conductive material can be employed, such as for example, metal or metal alloy. Electrically conductive materials include copper, brass, nickel, zinc, chromium, stainless steel, conductive plastics and rubbers, aluminum, semitransparent aluminum, steel, cadmium, silver, gold, zirconium, niobium, tantalum, vanadium, hafnium, titanium, nickel, niobium, stainless steel, chromium, tungsten, molybdenum, paper rendered conductive by the inclusion of a suitable material therein or through conditioning in a humid atmosphere to ensure the presence of sufficient water content to render the material conductive, indium, tin, metal oxides, including tin oxide and indium tin oxide, and the like. It could be a single metallic compound or dual layers of different metals and/or oxides.

The substrate 10 can also be formulated entirely of an electrically conductive material, or it can be an insulating material including inorganic or organic polymeric materials, such as MYLAR, a commercially available biaxially oriented polyethylene terephthalate from DuPont, or polyethylene naphthalate available as KALEDEX 2000, with a ground plane layer 12 comprising a conductive titanium or titanium/zirconium coating, otherwise a layer of an organic or inorganic material having a semiconductive surface layer, such as indium tin oxide, aluminum, titanium, and the like, or exclusively be made up of a conductive material such as, aluminum, chromium, nickel, brass, other metals and the like. The thickness of the support substrate depends on numerous factors, including mechanical performance and economic considerations.

The substrate 10 may have a number of many different configurations, such as for example, a plate, a cylinder, a drum, a scroll, an endless flexible belt, and the like. In the case of the substrate being in the form of a belt, as shown in FIG. 2, the belt can be seamed or seamless. In embodiments, the photoreceptor herein is in a drum configuration.

The thickness of the substrate 10 depends on numerous factors, including flexibility, mechanical performance, and economic considerations. The thickness of the support substrate 10 of the present embodiments may be at least about 500 micrometers, or no more than about 3,000 micrometers, or be at least about 750 micrometers, or no more than about 2500 micrometers.

An exemplary substrate support 10 is not soluble in any of the solvents used in each coating layer solution, is optically transparent or semi-transparent, and is thermally stable up to a high temperature of about 150° C. A substrate support 10 used for imaging member fabrication may have a thermal contraction coefficient ranging from about $1 \times 10^{-5}$ per ° C. to about $3 \times 10^{-5}$ per ° C. and a Young's Modulus of between about $5 \times 10^{-5}$ psi ($3.5 \times 10^{-4}$ Kg/cm$^2$) and about $7 \times 10^{-5}$ psi ($4.9 \times 10^{-4}$ Kg/cm$^2$).

The Ground Plane

The electrically conductive ground plane 12 may be an electrically conductive metal layer which may be formed, for example, on the substrate 10 by any suitable coating technique, such as a vacuum depositing technique. Metals include aluminum, zirconium, niobium, tantalum, vanadium, hafnium, titanium, nickel, stainless steel, chromium, tungsten, molybdenum, and other conductive substances, and mixtures thereof. The conductive layer may vary in thickness over substantially wide ranges depending on the optical transparency and flexibility desired for the electrophotoconductive member. Accordingly, for a flexible photoresponsive imaging device, the thickness of the conductive layer may be at least about 20 Angstroms, or no more than about 750 Angstroms, or at least about 50 Angstroms, or no more than about 200 Angstroms for an optimum combination of electrical conductivity, flexibility and light transmission.

Regardless of the technique employed to form the metal layer, a thin layer of metal oxide forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer. Generally, for rear erase exposure, a conductive layer light transparency of at least about 15 percent is desirable. The conductive layer need not be limited to metals. Other examples of conductive layers may be combinations of materials such as conductive indium tin oxide as a transparent layer for light having a wavelength between about 4000 Angstroms and about 9000 Angstroms or a conductive carbon black dispersed in a polymeric binder as an opaque conductive layer.

The Hole Blocking Layer

After deposition of the electrically conductive ground plane layer, the hole blocking layer 14 may be applied thereto. Electron blocking layers for positively charged photoreceptors allow holes from the imaging surface of the photoreceptor to migrate toward the conductive layer. For negatively charged photoreceptors, any suitable hole blocking layer capable of forming a barrier to prevent hole injection from the conductive layer to the opposite photoconductive layer may be utilized. The hole blocking layer may include polymers such as polyvinylbutryral, epoxy resins, polyesters, polysiloxanes, polyamides, polyurethanes and the like, or may be nitrogen containing siloxanes or nitrogen containing titanium compounds such as trimethoxysilyl propylene diamine, hydrolyzed trimethoxysilyl propyl ethylene diamine, N-beta-(aminoethyl) gamma-amino-propyl trimethoxy silane, isopropyl 4-aminobenzene sulfonyl, di(dodecylbenzene sulfonyl)titanate, isopropyl di(4-aminobenzoyl)isostearoyl titanate, isopropyl tri(N-ethylamino-ethylamino)titanate, isopropyl trianthranil titanate, isopropyl tri(N,N-dimethylethylamino)titanate, titanium-4-amino benzene sulfonate oxyacetate, titanium 4-aminobenzoate isostearate oxyacetate, $[H_2N(CH_2)_4]CH_3Si(OCH_3)_2$, (gamma-aminobutyl) methyl diethoxysilane, and $[H_2N(CH_2)_3]CH_3Si(OCH_3)_2$ (gamma-aminopropyl)methyl diethoxysilane.

General embodiments of the undercoat layer may comprise a metal oxide and a resin binder. The metal oxides that can be used with the embodiments herein include, but are not limited to, titanium oxide, zinc oxide, tin oxide, aluminum oxide, silicon oxide, zirconium oxide, indium oxide, molybdenum oxide, and mixtures thereof. Undercoat layer binder materials may include, for example, polyesters, MOR-ESTER 49,000 from Morton International Inc., VITEL PE-100, VITEL PE-200, VITEL PE-200D, and VITEL PE-222 from Goodyear Tire and Rubber Co., polyarylates such as ARDEL from AMOCO Production Products, polysulfone from AMOCO Production Products, polyurethanes, and the like.

The hole blocking layer should be continuous and have a thickness of less than about 0.5 micrometer because greater thicknesses may lead to undesirably high residual voltage. A hole blocking layer of between about 0.005 micrometer and about 0.3 micrometer is used because charge neutralization after the exposure step is facilitated and optimum electrical performance is achieved. A thickness of between about 0.03 micrometer and about 0.06 micrometer is used for hole blocking layers for optimum electrical behavior. The hole blocking layers that contain metal oxides such as zinc oxide, titanium oxide, or tin oxide, may be thicker, for example, having a thickness up to about 25 micrometers. The blocking layer may be applied by any suitable conventional technique such as spraying, dip coating, draw bar coating, gravure coating, silk screening, air knife coating, reverse roll coating, vacuum deposition, chemical treatment and the like. For convenience in obtaining thin layers, the blocking layer is applied in the form of a dilute solution, with the solvent being removed after deposition of the coating by conventional techniques such as by vacuum, heating and the like. Generally, a weight ratio of between about 0.05:100 to about 0.5:100 for the hole blocking layer material and solvent is satisfactory for spray coating.

The Charge Generation Layer

The charge generation layer 18 may thereafter be applied to the undercoat layer 14. Any suitable charge generation binder including a charge generating/photoconductive material, which may be in the form of particles and dispersed in a film forming binder, such as an inactive resin, may be utilized. Examples of charge generating materials include, for example, inorganic photoconductive materials such as amorphous selenium, trigonal selenium, and selenium alloys selected from the group consisting of selenium-tellurium, selenium-tellurium-arsenic, selenium arsenide and mixtures thereof, and organic photoconductive materials including various phthalocyanine pigments such as the X-form of metal free phthalocyanine, metal phthalocyanines such as vanadyl phthalocyanine and copper phthalocyanine, hydroxy gallium phthalocyanines, chlorogallium phthalocyanines, titanyl phthalocyanines, quinacridones, dibromo anthanthrone pigments, benzimidazole perylene, substituted 2,4-diamino-triazines, polynuclear aromatic quinones, enzimidazole perylene, and the like, and mixtures thereof, dispersed in a film forming polymeric binder. Selenium, selenium alloy, benzimidazole perylene, and the like and mixtures thereof may be formed as a continuous, homogeneous charge generation layer. Benzimidazole perylene compositions are well known and described, for example, in U.S. Pat. No. 4,587,189, the entire disclosure thereof being incorporated herein by reference. Multi-charge generation layer compositions may be used where a photoconductive layer enhances or reduces the properties of the charge generation layer. Other suitable charge generating materials known in the art may also be utilized, if desired. The charge generating materials selected should be sensitive to activating radiation having a wavelength between about 400 and about 900 nm during the imagewise radiation exposure step in an electrophotographic imaging process to form an electrostatic latent image. For example, hydroxygallium phthalocyanine absorbs light of a wavelength of from about 370 to about 950 nanometers, as disclosed, for example, in U.S. Pat. No. 5,756,245.

Any suitable inactive resin materials may be employed as a binder in the charge generation layer 18, including those described, for example, in U.S. Pat. No. 3,121,006, the entire disclosure thereof being incorporated herein by reference. Organic resinous binders include thermoplastic and thermosetting resins such as one or more of polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl butyral, polyvinyl acetate, polysiloxanes, polyacrylates, polyvinyl acetals, polyamides, polyimides, amino resins, phenylene oxide resins, terephthalic acid resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride/vinylchloride copolymers, vinylacetate/vinylidene chloride copolymers, styrene-alkyd resins, and the like. Another film-forming polymer binder is PCZ-400 (poly (4,4'-dihydroxy-diphenyl-1-1-cyclohexane) which has a viscosity-molecular weight of 40,000 and is available from Mitsubishi Gas Chemical Corporation (Tokyo, Japan).

The charge generating material can be present in the resinous binder composition in various amounts. Generally, at least about 5 percent by volume, or no more than about 90 percent by volume of the charge generating material is dispersed in at least about 95 percent by volume, or no more than about 10 percent by volume of the resinous binder, and more specifically at least about 20 percent, or no more than about 60 percent by volume of the charge generating material is dispersed in at least about 80 percent by volume, or no more than about 40 percent by volume of the resinous binder composition.

In specific embodiments, the charge generation layer 18 may have a thickness of at least about 0.1 µm, or no more than about 2 µm, or of at least about 0.2 µm, or no more than about 1 µm. These embodiments may be comprised of chlorogallium phthalocyanine or hydroxygallium phthalocyanine or mixtures thereof. The charge generation layer 18 containing the charge generating material and the resinous binder material generally ranges in thickness of at least about 0.1 µm, or no more than about 5 µm, for example, from about 0.2 µm to about 3 µm when dry. The charge generation layer thickness is generally related to binder content. Higher binder content compositions generally employ thicker layers for charge generation.

The Charge Transport Layer

In a drum photoreceptor, the charge transport layer comprises a single layer of the same composition. As such, the charge transport layer will be discussed specifically in terms of a single layer 20, but the details will be also applicable to an embodiment having dual charge transport layers. The charge transport layer 20 is thereafter applied over the charge generation layer 18 and may include any suitable transparent organic polymer or non-polymeric material capable of supporting the injection of photogenerated holes or electrons from the charge generation layer 18 and capable of allowing the transport of these holes/electrons through the charge transport layer to selectively discharge the surface charge on the imaging member surface. In one embodiment, the charge transport layer 20 not only serves to transport holes, but also protects the charge generation layer 18 from abrasion or chemical attack and may therefore extend the service life of the imaging member. The charge transport layer 20 can be a substantially non-photoconductive material, but one which supports the injection of photogenerated holes from the charge generation layer 18.

The layer 20 is normally transparent in a wavelength region in which the electrophotographic imaging member is to be used when exposure is affected there to ensure that most of the incident radiation is utilized by the underlying charge generation layer 18. The charge transport layer should exhibit excellent optical transparency with negligible light absorp tion and no charge generation when exposed to a wavelength of light useful in xerography, e.g., 400 to 900 nanometers. In the case when the photoreceptor is prepared with the use of a transparent substrate 10 and also a transparent or partially transparent conductive layer 12, image wise exposure or erasure may be accomplished through the substrate 10 with all light passing through the back side of the substrate. In this case, the materials of the layer 20 need not transmit light in the wavelength region of use if the charge generation layer 18 is sandwiched between the substrate and the charge transport layer 20. The charge transport layer 20 in conjunction with the charge generation layer 18 is an insulator to the extent that an electrostatic charge placed on the charge transport layer is not conducted in the absence of illumination. The charge transport layer 20 should trap minimal charges as the charge passes through it during the discharging process.

The charge transport layer 20 may include any suitable charge transport component or activating compound useful as an additive dissolved or molecularly dispersed in an electrically inactive polymeric material, such as a polycarbonate binder, to form a solid solution and thereby making this material electrically active. "Dissolved" refers, for example, to forming a solution in which the small molecule is dissolved in the polymer to form a homogeneous phase; and molecularly dispersed in embodiments refers, for example, to charge transporting molecules dispersed in the polymer, the small molecules being dispersed in the polymer on a molecular scale. The charge transport component may be added to a film forming polymeric material which is otherwise incapable of supporting the injection of photogenerated holes from the charge generation material and incapable of allowing the transport of these holes. This addition converts the electrically inactive polymeric material to a material capable of supporting the injection of photogenerated holes from the charge generation layer 18 and capable of allowing the transport of these holes through the charge transport layer 20 in order to discharge the surface charge on the charge transport layer. The high mobility charge transport component may comprise small molecules of an organic compound which cooperate to transport charge between molecules and ultimately to the surface of the charge transport layer. For example, but not limited to, N,N'-diphenyl-N,N-bis(3-methylphenyl)-1,1'-biphenyl-4,4'-diamine (TPD), other arylamines like triphenyl amine, N,N,N',N'-tetra-p-tolyl-1,1'-biphenyl-4,4'-diamine (TM-TPD), and the like.

A number of charge transport compounds can be included in the charge transport layer, which layer generally is of a thickness of from about 5 to about 75 micrometers, and more specifically, of a thickness of from about 15 to about 40 micrometers. Examples of charge transport components are aryl amines of the following formulas/structures:

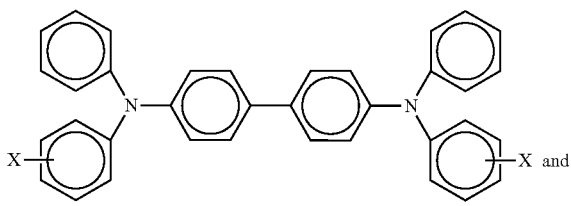

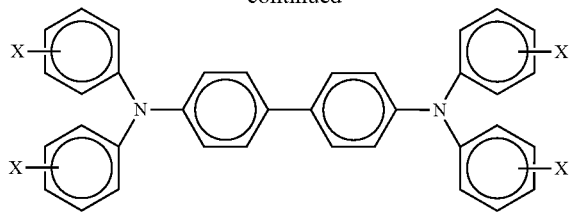

wherein X is a suitable hydrocarbon like alkyl, alkoxy, aryl, and derivatives thereof; a halogen, or mixtures thereof, and especially those substituents selected from the group consisting of Cl and $CH_3$; and molecules of the following formulas

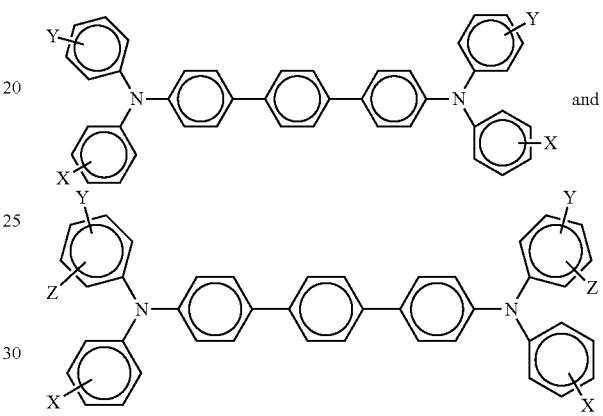

wherein X, Y and Z are independently alkyl, alkoxy, aryl, a halogen, or mixtures thereof, and wherein at least one of Y and Z are present.

Alkyl and alkoxy contain, for example, from 1 to about 25 carbon atoms, and more specifically, from 1 to about 12 carbon atoms, such as methyl, ethyl, propyl, butyl, pentyl, and the corresponding alkoxides. Aryl can contain from 6 to about 36 carbon atoms, such as phenyl, and the like. Halogen includes chloride, bromide, iodide, and fluoride. Substituted alkyls, alkoxys, and aryls can also be selected in embodiments.

Examples of specific aryl amines that can be selected for the charge transport layer include N,N'-diphenyl-N,N'-bis(alkylphenyl)-1,1-biphenyl-4,4'-diamine wherein alkyl is selected from the group consisting of methyl, ethyl, propyl, butyl, hexyl, and the like; N,N'-diphenyl-N,N'-bis(halophenyl)-1,1'-biphenyl-4,4'-diamine wherein the halo substituent is a chloro substituent; N,N'-bis(4-butylphenyl)-N,N'-di-p-tolyl-[p-terphenyl]-4,4''-diamine, N,N'-bis(4-butylphenyl)-N,N'-di-m-tolyl-[p-terphenyl]-4,4''-diamine, N,N'-bis(4-butylphenyl)-N,N'-di-o-tolyl-[p-terphenyl]-4,4''-diamine, N,N'-bis(4-butylphenyl)-N,N'-bis-(4-isopropylphenyl)-[p-terphenyl]-4,4''-diamine, N,N'-bis(4-butylphenyl)-N,N'-bis-(2-ethyl-6-methylphenyl)-[p-terphenyl]-4,4''-diamine, N,N'-bis(4-butylphenyl)-N,N'-bis-(2,5-dimethylphenyl)-[p-terphenyl]-4,4'-diamine, N,N'-diphenyl-N,N'-bis(3-chlorophenyl)-[p-terphenyl]-4,4''-diamine, and the like. Other known charge transport layer molecules may be selected in embodiments, reference for example, U.S. Pat. Nos. 4,921,773 and 4,464,450, the disclosures of which are totally incorporated herein by reference in their entirety.

Examples of the binder materials selected for the charge transport layers include components, such as those described in U.S. Pat. No. 3,121,006, the disclosure of which is totally incorporated herein by reference in its entirety. Specific examples of polymer binder materials include polycarbonates, polyarylates, acrylate polymers, vinyl polymers, cellulose polymers, polyesters, polysiloxanes, polyamides, polyurethanes, poly(cyclo olefins), and epoxies, and random or alternating copolymers thereof. In embodiments, the charge transport layer, such as a hole transport layer, may have a thickness of at least about 10 µm, or no more than about 40 µm.

Examples of components or materials optionally incorporated into the charge transport layers or at least one charge transport layer to, for example, enable improved lateral charge migration (LCM) resistance include hindered phenolic antioxidants such as tetrakis methylene(3,5-di-tert-butyl-4-hydroxy hydrocinnamate) methane (IRGANOX® 1010, available from Ciba Specialty Chemical), butylated hydroxytoluene (BHT), and other hindered phenolic antioxidants including SUMILIZER™ BHT-R, MDP-S, BBM-S, WX-R, NR, BP-76, BP-101, GA-80, GM and GS (available from Sumitomo Chemical Co., Ltd.), IRGANOX® 1035, 1076, 1098, 1135, 1141, 1222, 1330, 1425WL, 1520L, 245, 259, 3114, 3790, 5057 and 565 (available from Ciba Specialties Chemicals), and ADEKA STAB™ AO-20, AO-30, AO-40, AO-50, AO-60, AO-70, AO-80 and AO-330 (available from Asahi Denka Co., Ltd.); hindered amine antioxidants such as SANOL™ LS-2626, LS-765, LS-770 and LS-744 (available from SANKYO CO., Ltd.), TINUVIN® 144 and 622LD (available from Ciba Specialties Chemicals), MARK™ LA57, LA67, LA62, LA68 and LA63 (available from Asahi Denka Co., Ltd.), and SUMILIZER® TPS (available from Sumitomo Chemical Co., Ltd.); thioether antioxidants such as SUMILIZER® TP-D (available from Sumitomo Chemical Co., Ltd); phosphite antioxidants such as MARK™ 2112, PEP-8, PEP-24G, PEP-36, 329K and HP-10 (available from Asahi Denka Co., Ltd.); other molecules such as bis(4-diethylamino-2-methylphenyl)phenylmethane (BDETPM), bis-[2-methyl-4-(N-2-hydroxyethyl-N-ethyl-aminophenyl)]-phenylmethane (DHTPM), and the like. The weight percent of the antioxidant in at least one of the charge transport layer is from about 0 to about 20, from about 1 to about 10, or from about 3 to about 8 weight percent.

The charge transport layer should be an insulator to the extent that the electrostatic charge placed on the hole transport layer is not conducted in the absence of illumination at a rate sufficient to prevent formation and retention of an electrostatic latent image thereon. The charge transport layer is substantially nonabsorbing to visible light or radiation in the region of intended use, but is electrically "active" in that it allows the injection of photogenerated holes from the photoconductive layer, that is the charge generation layer, and allows these holes to be transported through itself to selectively discharge a surface charge on the surface of the active layer.

In addition, in the present embodiments using a belt configuration, the charge transport layer may consist of a single pass charge transport layer or a dual pass charge transport layer (or dual layer charge transport layer) with the same or different transport molecule ratios. In these embodiments, the dual layer charge transport layer has a total thickness of from about 10 µm to about 40 µm. In other embodiments, each layer of the dual layer charge transport layer may have an individual thickness of from 2 µm to about 20 µm. Moreover, the charge transport layer may be configured such that it is used as a top layer of the photoreceptor to inhibit crystallization at the interface of the charge transport layer and the overcoat layer. In another embodiment, the charge transport layer may be configured such that it is used as a first pass charge transport layer to inhibit microcrystallization occurring at the interface between the first pass and second pass layers.

Any suitable and conventional technique may be utilized to form and thereafter apply the charge transport layer mixture to the supporting substrate layer. The charge transport layer may be formed in a single coating step or in multiple coating steps. Dip coating, ring coating, spray, gravure or any other drum coating methods may be used.

Drying of the deposited coating may be effected by any suitable conventional technique such as oven drying, infra red radiation drying, air drying and the like. The thickness of the charge transport layer after drying is from about 10 µm to about 40 µm or from about 12 µm to about 36 µm for optimum photoelectrical and mechanical results. In another embodiment the thickness is from about 14 µm to about 36 µm.

The Adhesive Layer

An optional separate adhesive interface layer may be provided in certain configurations, such as for example, in flexible web configurations. In the embodiment illustrated in FIG. 1, the interface layer would be situated between the blocking layer 14 and the charge generation layer 18. The interface layer may include a copolyester resin. Exemplary polyester resins which may be utilized for the interface layer include polyarylatepolyvinylbutyrals, such as ARDEL POLYARYLATE (U-100) commercially available from Toyota Hsutsu Inc., VITEL PE-100, VITEL PE-200, VITEL PE-200D, and VITEL PE-222, all from Bostik, 49,000 polyester from Rohm Hass, polyvinyl butyral, and the like. The adhesive interface layer may be applied directly to the hole blocking layer 14. Thus, the adhesive interface layer in embodiments is in direct contiguous contact with both the underlying hole blocking layer 14 and the overlying charge generator layer 18 to enhance adhesion bonding to provide linkage. In yet other embodiments, the adhesive interface layer is entirely omitted.

Any suitable solvent or solvent mixtures may be employed to form a coating solution of the polyester for the adhesive interface layer. Solvents may include tetrahydrofuran, toluene, monochlorobenzene, methylene chloride, cyclohexanone, and the like, and mixtures thereof. Any other suitable and conventional technique may be used to mix and thereafter apply the adhesive layer coating mixture to the hole blocking layer. Application techniques may include spraying, dip coating, roll coating, wire wound rod coating, and the like. Drying of the deposited wet coating may be effected by any suitable conventional process, such as oven drying, infra red radiation drying, air drying, and the like.

The adhesive interface layer may have a thickness of at least about 0.01 micrometers, or no more than about 900 micrometers after drying. In embodiments, the dried thickness is from about 0.03 micrometers to about 1 micrometer.

The Ground Strip

The ground strip may comprise a film forming polymer binder and electrically conductive particles. Any suitable electrically conductive particles may be used in the electrically conductive ground strip layer 19. The ground strip 19 may comprise materials which include those enumerated in U.S. Pat. No. 4,664,995. Electrically conductive particles include carbon black, graphite, copper, silver, gold, nickel, tantalum, chromium, zirconium, vanadium, niobium, indium tin oxide and the like. The electrically conductive particles may have any suitable shape. Shapes may include irregular, granular, spherical, elliptical, cubic, flake, filament, and the like. The electrically conductive particles should have a particle size less than the thickness of the electrically conductive ground strip layer to avoid an electrically conductive ground strip layer having an excessively irregular outer surface. An average particle size of less than about 10 micrometers generally avoids excessive protrusion of the electrically conductive particles at the outer surface of the dried ground strip layer and ensures relatively uniform dispersion of the particles throughout the matrix of the dried ground strip layer. The concentration of the conductive particles to be used in the ground strip depends on factors such as the conductivity of the specific conductive particles utilized.

The ground strip layer may have a thickness of at least about 7 micrometers, or no more than about 42 micrometers, or of at least about 14 micrometers, or no more than about 27 micrometers.

The Anti-Curl Back Coating Layer

The anti-curl back coating 1 may comprise organic polymers or inorganic polymers that are electrically insulating or slightly semi-conductive. The anti-curl back coating provides flatness and/or abrasion resistance.

Anti-curl back coating 1 may be formed at the back side of the substrate 2, opposite to the imaging layers. The anti-curl back coating may comprise a film forming resin binder and an adhesion promoter additive. The resin binder may be the same resins as the resin binders of the charge transport layer discussed above. Examples of film forming resins include polyacrylate, polystyrene, bisphenol polycarbonate, poly(4,4'-isopropylidene diphenyl carbonate), 4,4'-cyclohexylidene diphenyl polycarbonate, and the like. Adhesion promoters used as additives include 49,000 (du Pont), Vitel PE-100, Vitel PE-200, Vitel PE-307 (Goodyear), and the like. Usually from about 1 to about 15 weight percent adhesion promoter is selected for film forming resin addition. The thickness of the anti-curl back coating is at least about 3 micrometers, or no more than about 35 micrometers, or about 14 micrometers.

Various exemplary embodiments encompassed herein include a method of imaging which includes generating an electrostatic latent image on an imaging member, developing a latent image, and transferring the developed electrostatic image to a suitable substrate.

While the description above refers to particular embodiments, it will be understood that many modifications may be made without departing from the spirit thereof. The accompanying claims are intended to cover such modifications as would fall within the true scope and spirit of embodiments herein.

While embodiments have been illustrated with respect to one or more implementations, alterations and/or modifications can be made to the illustrated examples without departing from the spirit and scope of the appended claims. In addition, while a particular feature herein may have been disclosed with respect to only one of several implementations, such feature may be combined with one or more other features of the other implementations as may be desired and advantageous for any given or particular function.

EXAMPLES

Preparation of the Double-Layer Composite Delivery Roller

The double layer composite delivery roller (FIG. 6) comprises two layers of an elastomeric matrix cast around a metal mandrel. The inner layer is composed of a paraffin-impregnated silicone polymer, and the outer layer is composed of only the silicone polymer or a paraffin-impregnated silicone polymer with a lower ratio than the inner layer. The inner paraffin-impregnated silicone layer was prepared by mixing paraffin oil into a cross-linkable, liquid polydimethylsiloxane (PDMS) before curing the PDMS polymer. The mixture (PDMS/paraffin oil) was cast onto the mandrel using a cylindrical mold, followed by curing. After curing, the PDMS/paraffin coated rod was extracted from the mold. The outer layer was prepared by curing the liquid, cross-linkable PDMS or a mixture of PDMS and parrifin around the inner PDMS/paraffin composite layer using a larger cylindrical mold in both length and diameter. PDMS was prepared by from a commercially available (Dow Corning Corporation), two-component system—a base and a curing agent. FIG. 6 is an image of a cross-section of a double layer roller. SEM images confirmed that the pores contained paraffin oil in the PDMS matrix of inner layer 41 of the roller.

Figure 7:
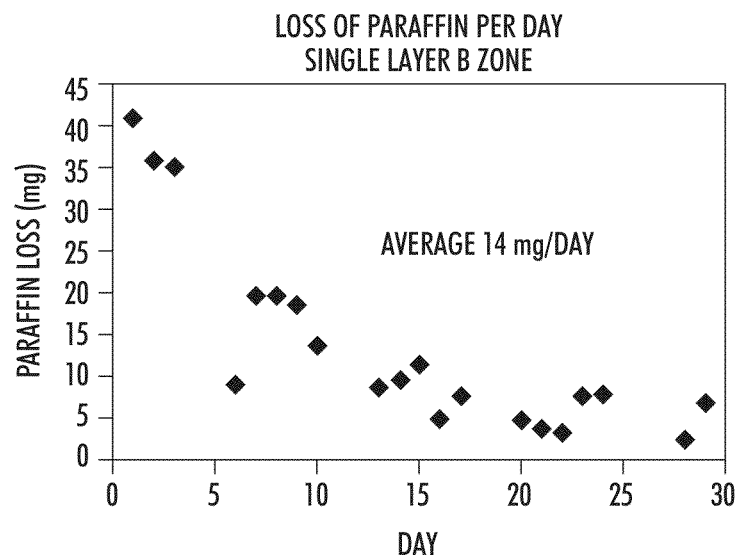
FIG. 7 shows the loss of paraffin oil from a single layer roller.
Figure 8:
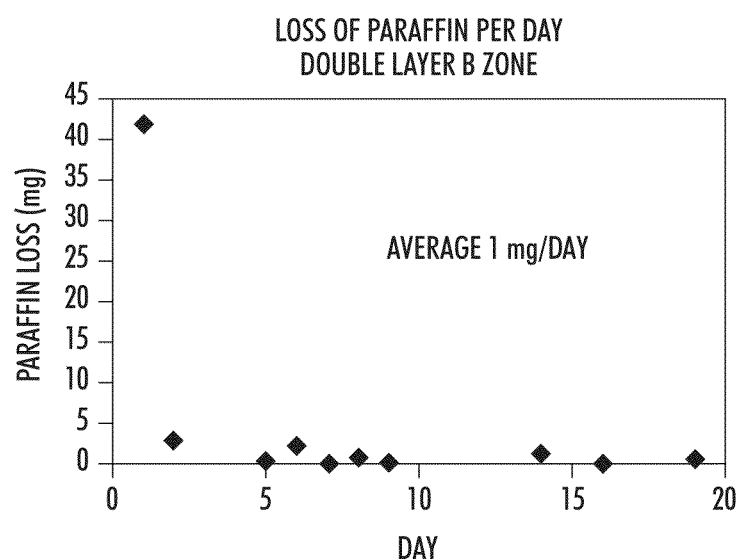
FIG. 8 shows the loss of paraffin oil from a double layer roller.

Single-layer and double-layer rollers were prepared to monitor the passive loss of paraffin from the roller over several days in different zones. The single-layer rollers (d=9 mm) were composed of 1:2 paraffin:PDMS and the double-layer rollers were composed of an inner layer (d=8 mm) of 1:2 paraffin:PDMS and an outer layer (d=9 mm) of only PDMS (i.e. the thickness of the outer layer was 0.5 mm). The passive loss of paraffin from rollers in each of A, B, and J-Zones was monitored by massing the rollers each day. In all zones, paraffin passively diffused from the single-layer rollers, although the amount decreased over time. The double-layer rollers prevented passive loss of paraffin in all zones. FIG. 7 shows the passive loss of paraffin over time from a single-layer delivery roller and FIG. 8 shows the loss of paraffin over-time from a double-layer delivery roller in B-Zone. The average loss of paraffin over 30 days for the single layer was 14 mg/day (FIG. 7). The double layer roller averaged a loss of less than 1 mg/day over 20 days (FIG. 8). In A-Zone, the average loss of paraffin from a single-layer roller was 25 mg/day and from a double-layer was less than 1 mg/day. In J-Zone, the average loss of paraffin from a single-layer roller was 7 mg/day and from a double-layer was less than 1 mg/day.

Machine Testing in an Olympia Machine

Figure 9:
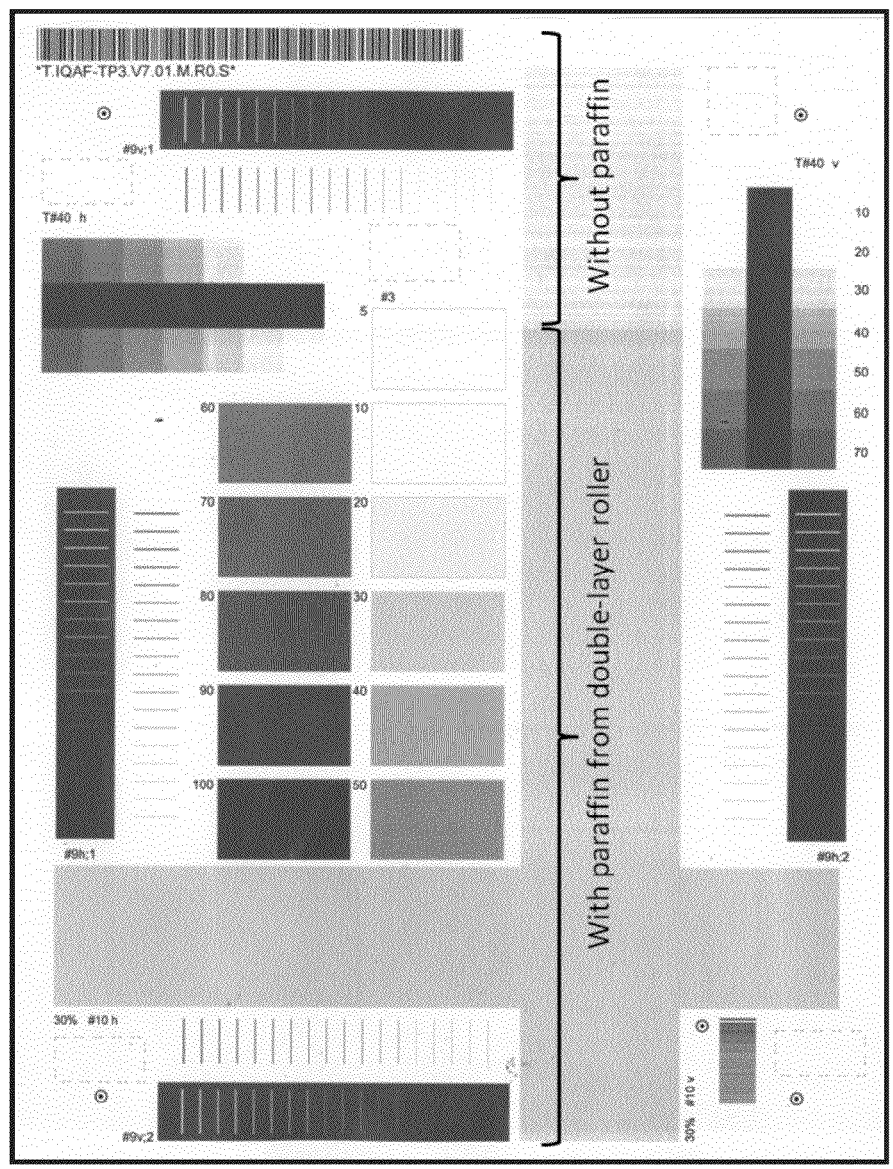
FIG. 9 is a print test comparison demonstrating A-zone deletion results of prints made with the system according to embodiments described herein and those made with a control system.

To compare image quality with and without paraffin, a double-layer PDMS paraffin delivery roller that spanned two thirds of the length of the photoreceptor (P/R) was used; this generated two thirds of the image with paraffin and a control region on the image without paraffin (5000 prints (12.5 kcycles) were completed). FIG. 9 is an image of a print obtained after 5000 prints (12.5 kcycles) using the double-layer composite roller with an overcoated (OCL) drum in A zone. FIG. 9 clearly shows that on regions where the paraffin oil was applied to the P/R the image has no defects, indicating that there were no adverse affects to the electrical properties of the P/R, and no torque issues. In comparison, the region without paraffin has both deletion and streaking defects. Image (T=5000, 12.5 kcycle) was obtained from an Olympia machine using an OCL drum in A-Zone and a double-layer composite delivery roller. The left side of the image from the two thirds of the P/R in contact with the delivery roller shows no image defects; the right side of the image from the one third of the P/R without the delivery roller shows A-Zone deletions and streaking (which is indicative of blade damage due to torque).

A summary of the results indicates a double-layer composite paraffin-impregnated PDMS delivery roller has the following benefits. The inner layer is a reservoir for the functional material (paraffin oil). The outer PDMS layer prevents the passive loss of paraffin when high fractions of paraffin oil are dispersed in PDMS. Integration of the double layer roller had no adverse affects on the electrical functioning of the P/R devices. Sufficient quantities of paraffin oil are still delivered to the P/R surface using a double-layer roller to improve image quality compared to the image quality when no paraffin oil is applied.

A composite delivery roller is composed of two layers, an inner layer that functions as a reservoir and an outer layer functions to control the release of the functional material in the reservoir and it also imparts robustness to the roller. The control of the passive loss of paraffin oil from highly loaded rollers leads to more efficient use of the functional material. Controlling the loss of paraffin oil increases the sustainability of the paraffin oil supply thereby increasing the lifetime of the roller. The application of the paraffin oil to the photoreceptor does not adversely affect the electrical properties of the P/R. The elastomeric nature of the roller can facilitate contact between the roller and the P/R. Torque testing indicates that lower torque is achieved when the composite roller is used to apply paraffin to an overcoated P/R. Print tests (5 kprints, 12.5 kcycles) successfully completed in A zone using a double-layer composite roller with a OCL P/R indicated that sufficient paraffin was delivered; the tests resulted in good images with no deletions or streaking, and no motor faults, indicating that torque was not an issue. The wear rate of a P/R is reduced when paraffin oil is applied.

Another problem associated with an organic OCL is A-Zone deletion. Mechanistic studies demonstrated that A-zone deletion is caused by: 1) the formation of hydrophilic chemical species on the surface of the photoreceptor due to high energy charging by the BCR; 2) adsorption of water onto the hydrophilic P/R surface in a humid environment; and 3) increase in the surface conductivity of the photoreceptor due to the absorbed water layer and toner contaminants. It is believed that high torque is also attributed to the surface chemistry. The double layer allows for a higher loading of paraffin oil in the inner layer which increases the internal reservoir. The double layer roller is capable of dispensing an adequate amount of paraffin oil to the surface of the P/R to: i) sufficiently reduce torque, and ii) maintain acceptable image quality. The composite delivery roller is easily fabricated in two steps: i) curing the inner roller composed of PDMS and paraffin oil, followed by ii) curing the outer portion of the roller composed of PDMS only or PDMS and paraffin oil (in a lower ratio than the inner layer). Both materials are inexpensive, commercially available, and non-toxic.

It will be appreciated that variants of the above-disclosed and other features and functions or alternatives thereof, may be combined into other different systems or applications. Various presently unforeseen or unanticipated alternatives, modifications, variations, or improvements therein may be subsequently made by those skilled in the art which are also encompassed by the following claims.

What is claimed is:

1. A delivery member for use in an image forming apparatus comprising:
    a support member,
    an inner layer comprising an elastomeric matrix and a functional material dispersed therein, the inner layer disposed on the support member; and
    an outer layer disposed on the inner layer wherein the functional material diffuses to a surface of the outer layer, wherein the outer layer comprises a functional material dispersed in the elastomeric matrix in a ratio lower than that of the inner layer.

2. The delivery member according to claim 1, wherein the elastomeric matrix comprises a material selected from the group consisting of polysiloxane, polyurethane, polyester, polyfluorosilioxanes, polyolefin, fluoroelastomer, synthetic rubber, natural rubber, and mixtures thereof.

3. The delivery member according to claim 1, wherein the functional material is selected from the group consisting of alkanes, fluoroalkanes, alkyl silanes, fluoroalkyl silanes alkoxy-silanes, siloxanes, glycols or polyglycols, mineral oil, synthetic oil, natural oil, and mixtures thereof.

4. The delivery member according to claim 1, wherein the functional material comprises a paraffin oil.

5. The delivery member according to claim 1, wherein the inner layer comprises a thickness of from about 1 mm to about 30 mm.

6. The delivery member according to claim 1, wherein the inner layer comprises pores having a size of from about 1 micron to about 50 microns.

7. The delivery member according to claim 1, wherein a weight ratio of the functional material to the elastomeric matrix is from about 1:10 to about 1:1.

8. The delivery member according to claim 1, wherein the outer layer comprises a thickness of from about 0.1 µm to about 1 mm.

9. The delivery member according to claim 1, wherein the outer layer comprises a polymer selected from the group consisting of polysiloxane, polyurethane, polyester, polyfluorosilioxanes, polyolefin, fluoroelastomer, synthetic rubber, natural rubber, and mixtures thereof.

10. The delivery member according to claim 1, wherein the outer layer comprises pores having a size of less than about 1 µm.

11. An image forming apparatus comprising:
    a) an imaging member having a charge retentive surface for developing an electrostatic latent image thereon, wherein the imaging member comprises:
        a substrate, and
        a photoconductive member disposed on the substrate;
    b) a charging unit for applying an electrostatic charge on the imaging member to a predetermined electric potential; and
    c) a delivery member disposed in contact with the surface of the imaging member or a surface of the charging unit, wherein the delivery member comprises:
        (i) a support member,
        (ii) an inner layer comprising a elastomeric matrix and a functional material dispersed therein, the inner layer disposed on the support member; and
        (iii) an outer layer disposed on the inner layer, wherein the delivery member provides a functional material to the charge retentive surface at a rate of about 1 ng/kcycle/cm$^2$ to about 10 mg/kcycle/cm$^2$.

12. The image forming apparatus according to claim 11, wherein the functional material comprises an alkane compound and the elastomeric matrix comprises a cross-linked polydimethylsiloxane (PDMS).

13. The image forming apparatus according to claim 11, wherein the inner layer comprises a thickness of from about 1 mm to about 30 mm.

14. The image forming apparatus according to claim 11, wherein the outer layer comprises a thickness of from about 0.1 µm to about 1 mm.

15. The image forming apparatus according to claim 11, wherein the outer layer comprises a polymer selected from the group consisting of polysiloxane, polyurethane, polyester, polyfluorosilioxanes, polyolefin, fluoroelastomer, synthetic rubber, natural rubber, and mixtures thereof.

16. A delivery member for use in an image forming apparatus comprising:
    a support member,
    an inner layer comprising an elastomeric matrix and a functional material dispersed therein, the inner layer disposed on the support member wherein the inner layer comprises pores having a size of from about 1 microns to about 50 microns; and an outer layer disposed on the inner layer wherein the outer layer comprises pores having a size of less than about 1 µm, wherein the outer layer comprises a functional material dispersed in the elastomeric matrix in a ratio lower than that of the inner layer.

17. The delivery member according to claim 16, wherein the functional material comprises paraffin oil.

* * * * *